(12) United States Patent
Wurzbach

(10) Patent No.: US 7,984,661 B2
(45) Date of Patent: Jul. 26, 2011

(54) GREASE SAMPLING KIT, GREASE SAMPLING DEVICES MADE FROM THE KIT, AND RELATED METHODS

(76) Inventor: Richard N. Wurzbach, Brogue, PA (US)

( * ) Notice: Subject to any disclaimer, the term of this patent is extended or adjusted under 35 U.S.C. 154(b) by 261 days.

(21) Appl. No.: 12/107,873

(22) Filed: Apr. 23, 2008

(65) Prior Publication Data

US 2009/0183580 A1 Jul. 23, 2009

Related U.S. Application Data

(60) Provisional application No. 61/022,404, filed on Jan. 21, 2008.

(51) Int. Cl.
*G01N 1/10* (2006.01)

(52) U.S. Cl. .................. 73/864.73; 73/864.44

(58) Field of Classification Search .................. None
See application file for complete search history.

(56) References Cited

U.S. PATENT DOCUMENTS

| | | | | |
|---|---|---|---|---|
| 1,878,610 | A | * | 9/1932 | Stern .......................... 73/864.64 |
| 1,883,021 | A | * | 10/1932 | Silknitter .................... 222/146.4 |
| 2,017,924 | A | * | 10/1935 | Smith .......................... 604/135 |
| 4,479,377 | A | * | 10/1984 | Jackson et al. ................. 73/1.19 |
| 4,744,255 | A | * | 5/1988 | Jaeger ......................... 73/863.84 |
| 4,925,496 | A | | 5/1990 | Stouky et al. |
| 5,001,805 | A | | 3/1991 | Stouky et al. |
| 5,052,827 | A | | 10/1991 | Huiskamp et al. |
| 5,392,632 | A | * | 2/1995 | Umeda et al. .................. 73/1.73 |
| 6,471,215 | B1 | | 10/2002 | Drago et al. |
| 7,114,367 | B1 | * | 10/2006 | Owens .......................... 73/1.19 |
| 2003/0115977 | A1 | * | 6/2003 | Holweg et al. ................ 73/865.9 |
| 2004/0116872 | A1 | * | 6/2004 | Odell et al. .................... 604/192 |

FOREIGN PATENT DOCUMENTS

| EP | 0430327 | * | 5/1991 |
|---|---|---|---|
| EP | 0982579 | * | 5/2007 |

OTHER PUBLICATIONS

Written Opinion of the International Search Authority in corresponding PCT application PCT/US2009/031416 (Korean Intellectual Property Office), Aug. 28, 2009, 8 pages.*
Bill Herguth, "Grease Analysis", Practicing Oil Analysis, Mar.-Apr. 2002, p. 18, 6 pages.
Surapol Raadnui, "Low-cost Used Grease Analysis for Rolling Element Bearings", http://www.practicingoilanalysis.com/article_detail.asp?articleid=672, visited Jan. 9, 2008, 7 pages.

* cited by examiner

*Primary Examiner* — Robert R Raevis
(74) *Attorney, Agent, or Firm* — Hooker & Habib, P.C.

(57) ABSTRACT

A kit of component parts for forming at least first and second grease sampling devices includes a number of housings, piston bodies, and piston shafts. A first grease sampling device has a piston movable in the barrel and vent holes that resists the buildup of back pressure when the device is filled with a grease sample. A second grease sampling device includes a push rod extending from the piston that enables a representative grease sample to be obtained from a bearing, gear or other lubricated part that is not easily accessible.

5 Claims, 7 Drawing Sheets

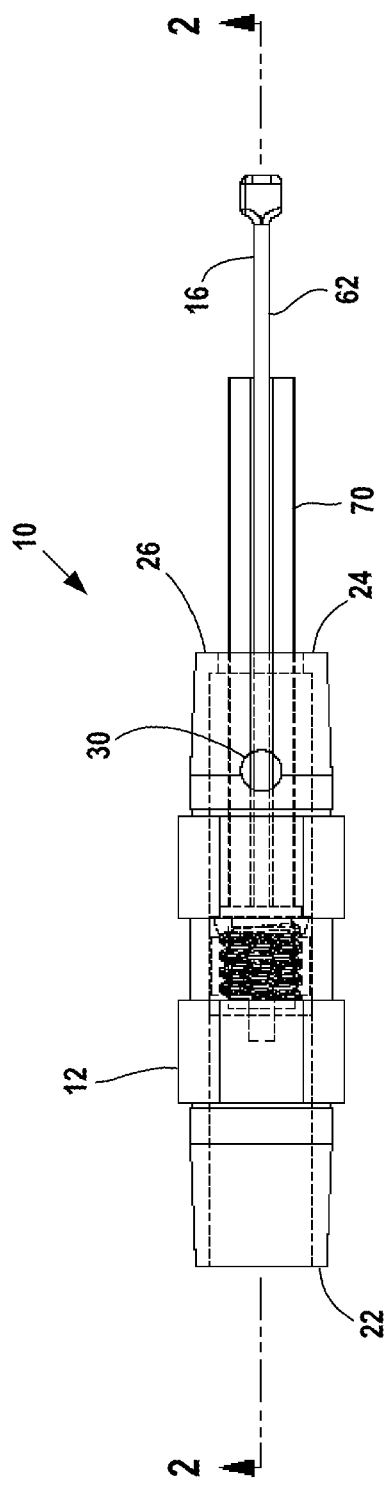
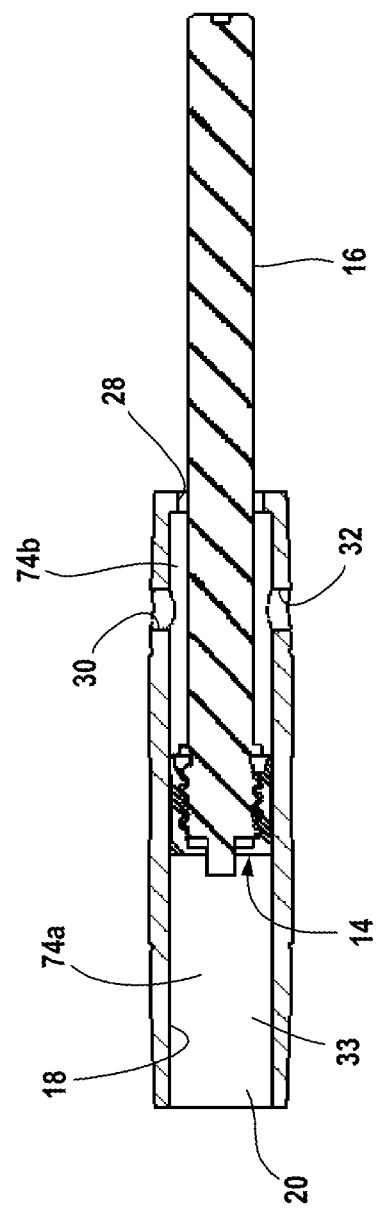

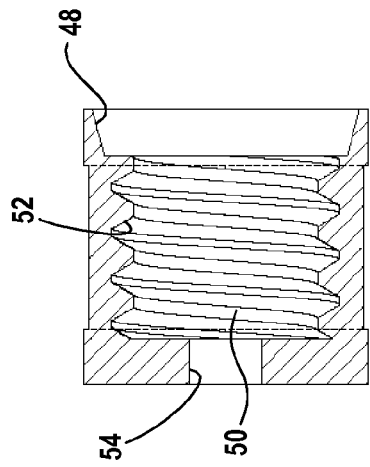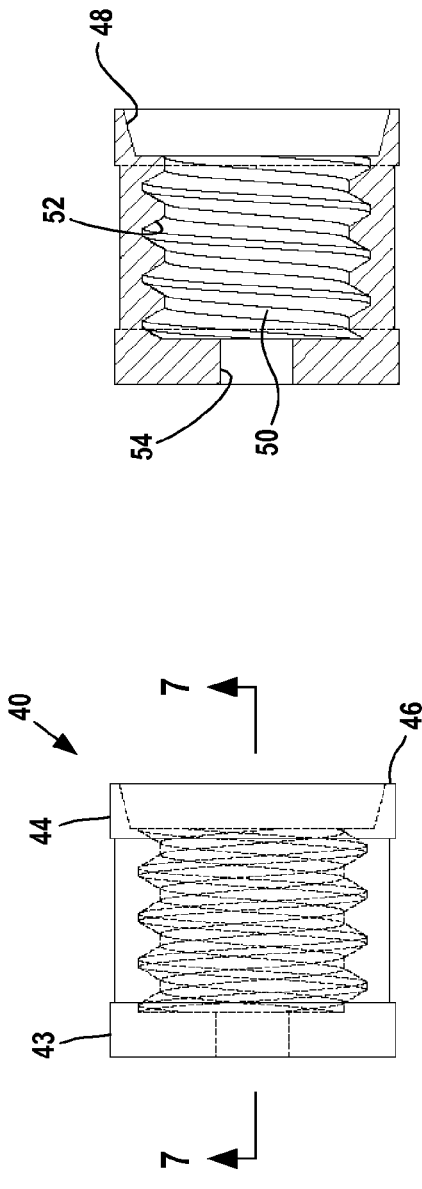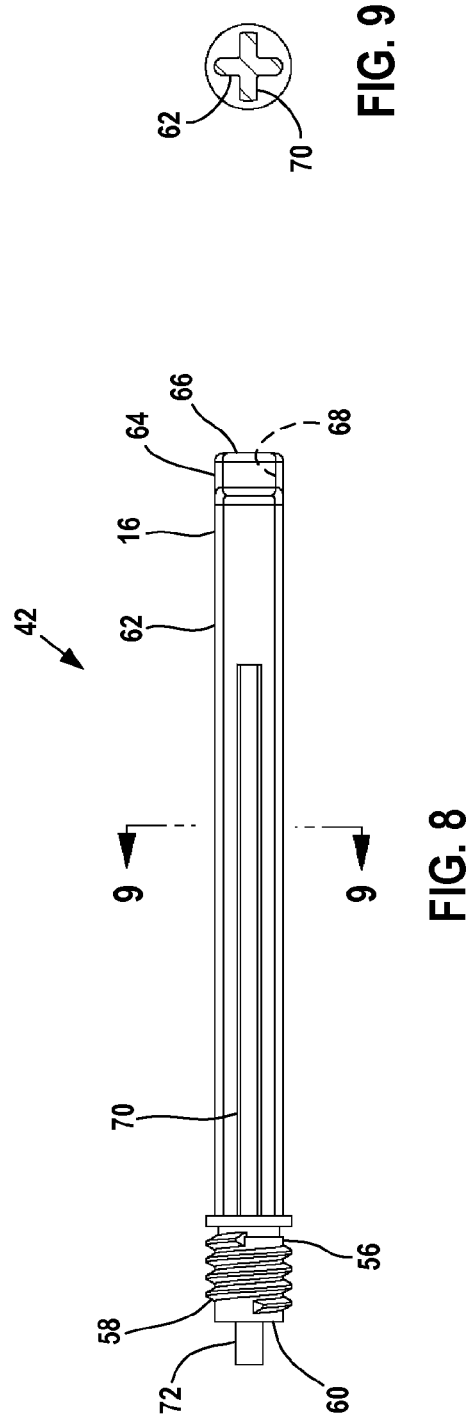

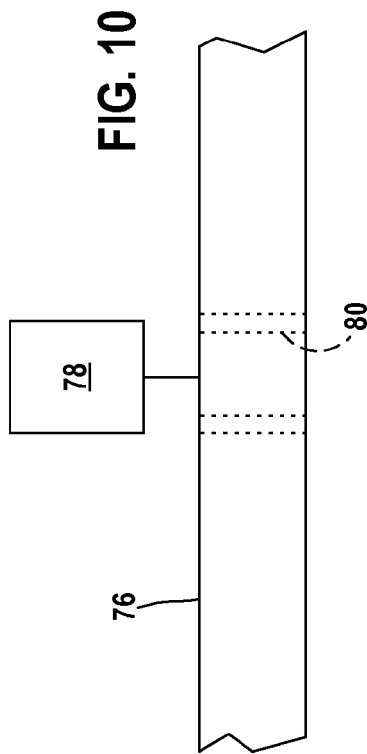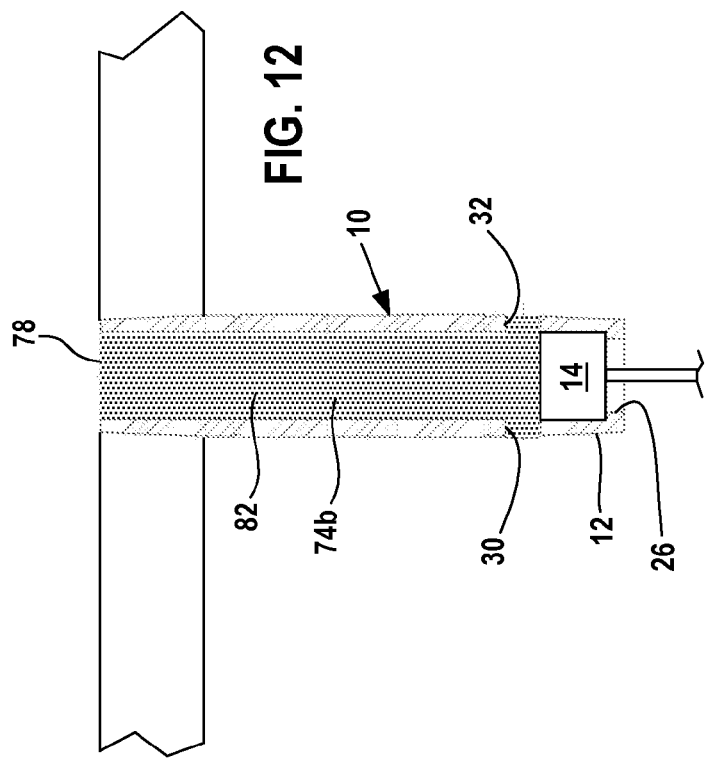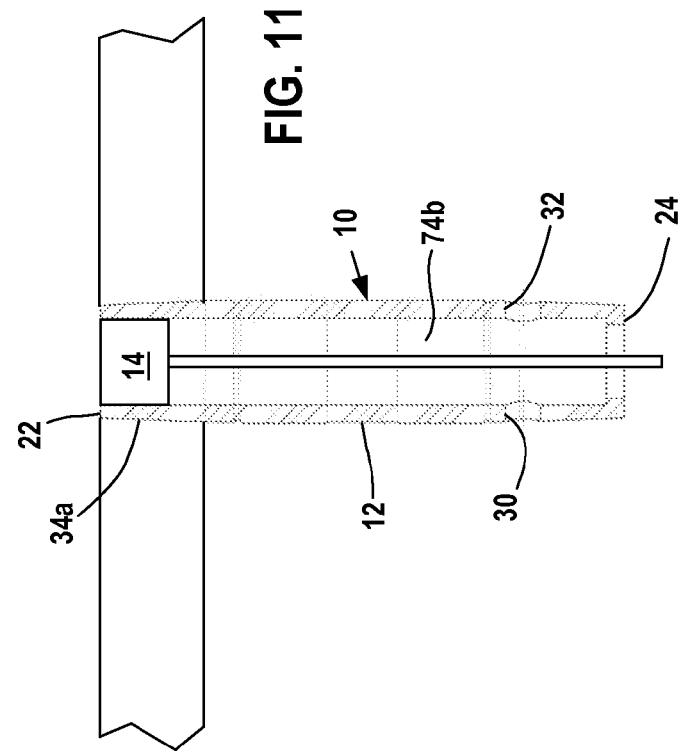

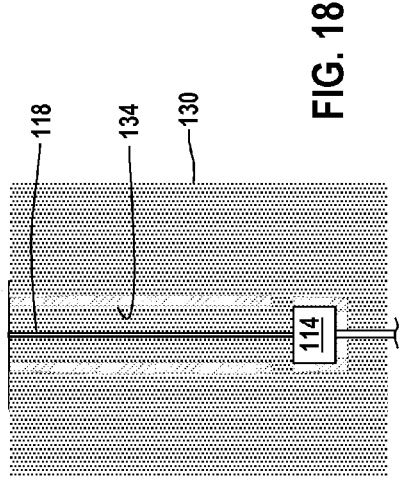
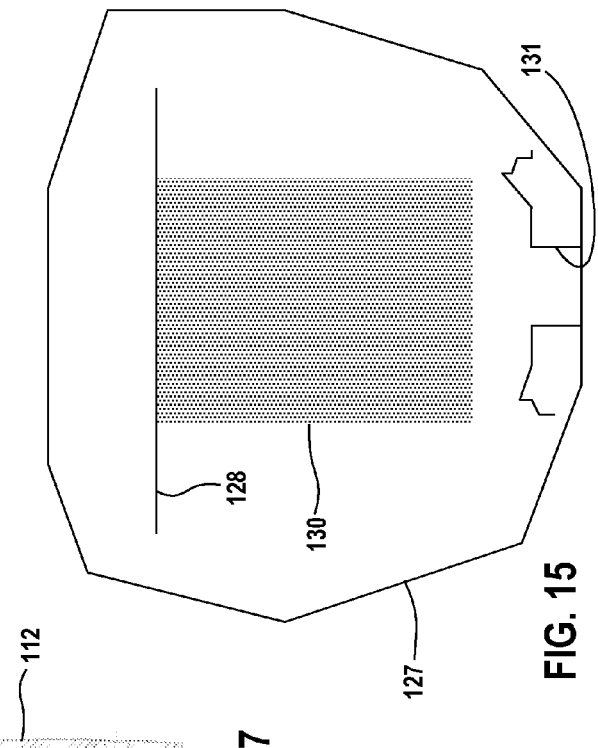
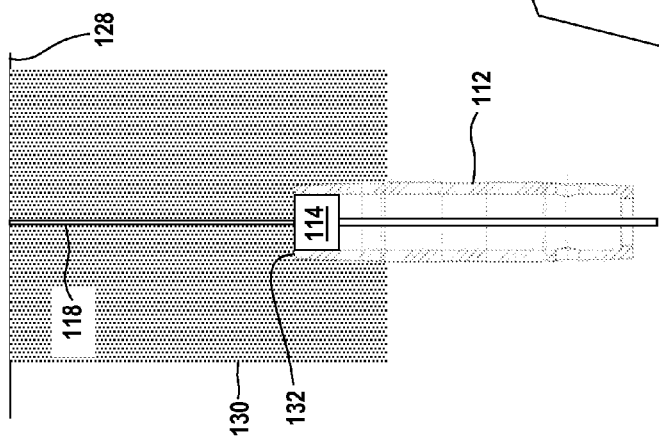
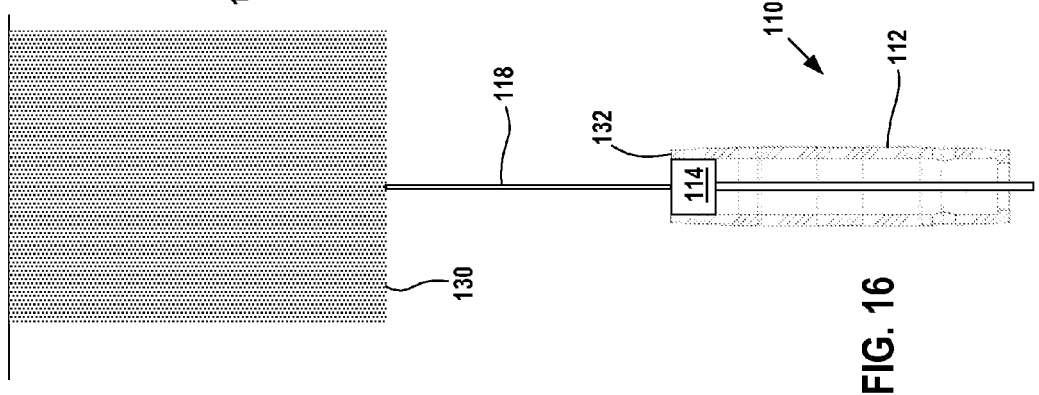

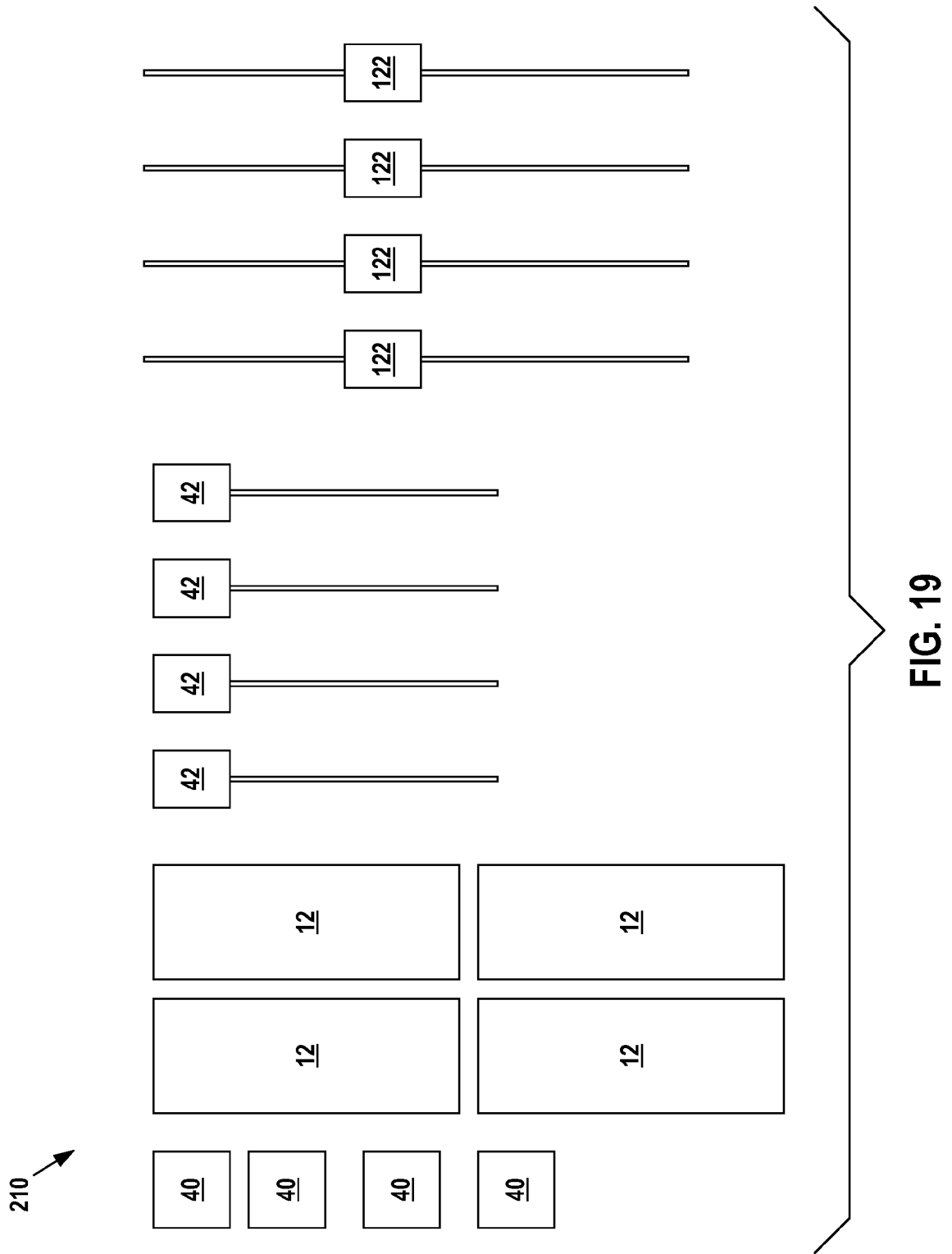

GREASE SAMPLING KIT, GREASE SAMPLING DEVICES MADE FROM THE KIT, AND RELATED METHODS

This application claims priority to my provisional patent application No. 61/022,404 filed Jan. 21, 2008.

FIELD OF THE INVENTION

The invention relates to devices for obtaining samples of lubricating grease from machine bearings, gears or other grease-lubricated components, a grease sampling kit having components for making such grease sampling devices, and related methods of obtaining grease samples from machine lubricated surfaces.

BACKGROUND OF THE INVENTION

It is estimated that 90% of all machine bearings are lubricated by grease. While oil analysis is a widespread tool for monitoring bearing and lubricated component health of important oil lubricated equipment, grease analysis is not generally adopted in a similar manner for important grease lubricated machines. Analyzing a sample of grease taken from a grease-lubricated bearing sometimes is performed to pinpoint the cause of bearing problems in failure analysis. However, the ability to adopt regular and routine grease analysis for important machines has been historically limited by the inability to easily obtain representative samples of the grease in a sufficient quantity to perform cost-effective and meaningful analysis.

Some machine bearings, such as pillow block bearings, may be located on the outside of the machine and may have an exposed layer or thickness of grease surrounding the bearing. A grease sample is obtained by scooping or scraping through the layer of grease. The grease nearest the bearing usually makes the most representative sample, and the scoop or scraper is manipulated to retrieve grease near the bearing. The grease sample, however, may be contaminated by grease retained by the scoop or scraper when moving through the layers of grease away from the bearing.

Other machine bearings may be located in areas of the machine that have limited access. This can make it difficult to manipulate a scoop or scraper in such away as to obtain only an uncontaminated grease sample taken near those surfaces.

Some machine bearings are housed inside the machine without external access. The housing may incorporate grease inlet openings and grease drain openings associated with the machine bearings. Historically, some efforts to obtain grease samples have been made by flowing fresh grease into a grease inlet until grease flows out a drain outlet. While this can sometimes be effective, there is a risk that the bearing may be overfilled with grease—damaging the bearing or lifting the bearing seals.

Thus there is a need for grease sampling devices that can obtain a representative grease sample from a bearing, gear or other internally mounted grease lubricated component. The devices should be usable in different bearing operating configurations for retrieving samples from exposed bearings, from bearings having limited access, or from bearings or other lubricated parts accessible via machine openings.

SUMMARY OF THE INVENTION

The present invention is a kit of component parts for forming a set of grease sampling devices for obtaining representative grease samples from bearings. The component parts enable a grease sampling device to be easily assembled that is suited for the particular configuration of the bearing from which the sample is to be obtained. The grease sampling devices of the present invention enable a representative grease sample to be efficiently obtained without harming the bearing or the bearing seals, and allow grease to be selectively sampled by obtaining the grease that is located closest to the lubricated part.

A first grease sampling device formed from the kit in accordance with the present invention includes an elongated tubular housing having an open housing end and a piston that slides in the housing. The piston divides the interior of the chamber into a first chamber adjacent the open housing end and an opposite second chamber adjacent the other housing end. A relief opening spaced from the other housing end extends through the housing wall and into the interior of the housing.

The relief opening communicates with the second housing chamber when the piston is adjacent the open end of the housing. The relief opening communicates with the first housing chamber when the piston is approximately in contact with the other end of the housing.

The open end of the housing can be attached to a grease drain opening while the machine is operating or shut down, with the piston at the open end of the housing. This places the open end of the housing in fluid communication with the bearing housing. With the machine in operation, pressurized grease might be forced through the drain opening and into the housing. The source of pressure in the grease may be either from the rotation of the bearing, or from the pumping of new grease into the reservoir. The grease flows into the housing and forces the piston towards the other end of the housing. When the piston moves past the relief opening, excess grease flows out the relief opening. Discharging excess grease relieves the pressure within the housing, preventing a buildup of back pressure when the housing is filled that might otherwise compromise the bearing seals, leading to bearing damage or entry of grease to undesired areas of the machine (such as motor windings).

In a preferred embodiment of the grease sampling device a piston rod extends from the piston and out the other end of the housing. The piston rod enables the grease sampling device to be used as a syringe to manually retrieve a grease sample when the grease is easily accessible. The piston is placed at the open end of the housing, and the open end of the housing is inserted into a thickness of grease. The piston closes the housing and prevents grease from entering the housing until the housing is near the bearing. Retracting the piston draws a representative sample of grease from near the bearing into the housing.

A second grease sampling device formed from the kit in accordance with the present invention is intended for use when the grease-lubricated components are less accessible. This is performed when the equipment in not operating or rotating. The second grease sampling device is similar to the first device but includes a push rod that extends from the piston and towards the open end of the housing. The piston is placed at the open end of the housing, and the open end of the housing is inserted into a thickness of grease. The piston prevents grease from entering the housing as before, and the housing is moved towards the bearing until the push rod comes into contact with a rigid bearing surface. Continued movement of the housing towards the bearing presses the push rod against the surface and forces the piston into the piston housing, drawing grease into the housing.

The component parts of the present invention includes a set of like housings for forming either the first or second grease sampling device, a set of like piston bodies, a set of like first piston shafts, and a set of second piston shafts. The component parts are preferably made from injection molded plastic. The grease sampling devices formed from the component parts are disposed of after use and are not re-used.

Each first piston shaft includes a piston rod and each second piston shaft includes a piston rod and a push rod. Each piston body can be removably attached to either a first piston shaft or a second piston shaft for assembling the first or second grease sampling device respectively. The piston shaft can be removed from the piston body after the housing is filled with grease to enable later analysis by forcing the grease out of the body by the piston, and preferably through a slotted cap.

The grease sampling devices of the present invention are inexpensive, easy to operate, and help ensure that representative grease samples are obtained. The component parts of the devices can be provided as a kit, enabling users to assemble the sampling device best suited for retrieving a particular grease sample. The piston may also be used to extrude the grease sample from the housing for testing or analysis.

Other objects and features of the invention will become apparent as the description proceeds, especially when taken in conjunction with the accompanying drawing sheets illustrating two grease sampling devices made from the kit and the operation of such devices.

BRIEF DESCRIPTION OF THE DRAWINGS

FIG. 1 is a side view of a first embodiment grease sampling device in accordance with the present invention;

FIG. 2 is a sectional view taken along line 2-2 of FIG. 1;

FIG. 6 is a side view of the piston body of the grease sampling device shown in FIG. 1;

FIG. 7 is a sectional view taken along line 7-7 of FIG. 6;

FIG. 8 is a bottom view of the piston shaft of the grease sampling device shown in FIG. 1;

FIG. 9 is a sectional view taken along line 9-9 of FIG. 8;

FIGS. 10-12 illustrate use of the grease sampling device shown in FIG. 1 to obtain a grease sample from a source of pressurized grease;

FIGS. 15-18 illustrate use of the grease sampling device shown in FIG. 13 to obtain a grease sample from adjacent a rigid bearing surface;

FIG. 19 illustrates the component parts of a grease sampling kit in accordance with the present invention.

DESCRIPTION OF THE PREFERRED EMBODIMENTS

Figure 4:
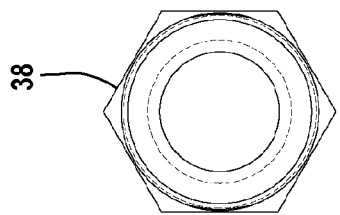
FIG. 4 is an end view of the housing shown in FIG. 3.

The invention is a grease sampling kit having component parts for making different types of grease sampling devices. The component parts are preferably made of plastic and manufactured by injection molding.

FIGS. 1 and 2 illustrate a first embodiment grease sampling device 10 formed from the kit's component parts. Grease sampling device 10 is intended for obtaining a grease sample from a source of pressurized grease as will be explained in greater detail later.

Grease sampling device 10 includes a tubular housing or barrel 12 and a piston 14 slideably mounted in the barrel. A piston rod 16 extends from one side of the piston 14 and out of the housing 12.

Housing 12 is preferably formed from a transparent plastic, and has an annular body or wall 18 that surrounds the housing bore 20. Housing 12 extends axially from an open housing end 22 to a partially closed housing end 24. End wall 26 closes housing end 24 and includes a coaxial opening 28 that receives the piston rod 16. A pair of through openings or vent holes 30, 32 extends through the housing body 18 and communicates the interior 33 of the housing 12 with the exterior. Openings 30, 32 are axially spaced away from the housing end 24 a distance slightly greater than the axial length of the piston 14.

Figure 3:
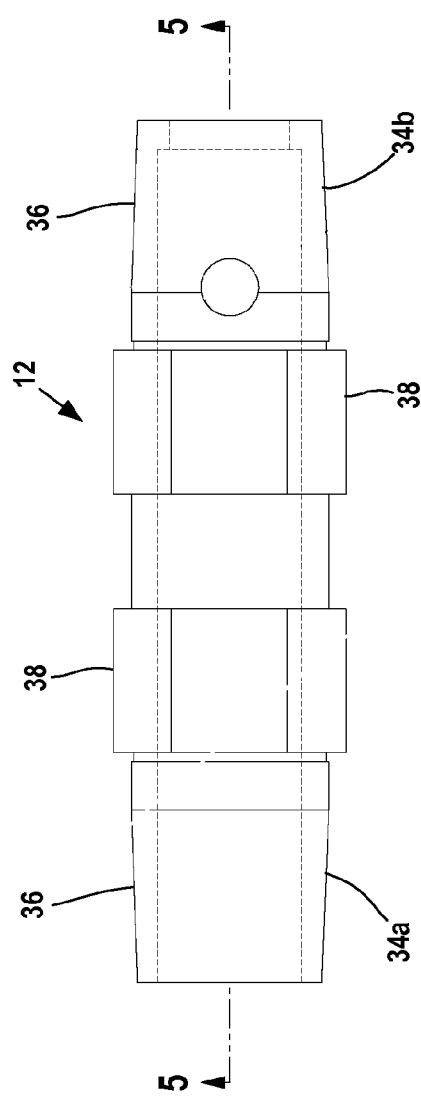
FIG. 3 is a side view of the tubular housing of the grease sampling device shown in FIG. 1.
Figure 5:
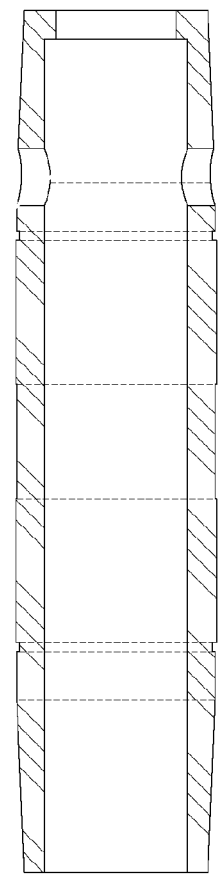
FIG. 5 is a sectional view taken along line 5-5 of FIG. 3.

Housing 12 has similar opposite end portions 34 that each includes external pipe threads 36. See FIGS. 3-5. Spaced inwardly from each threaded housing end portion 34 is an intermediate body portion 38. Each body portion 38 has a hexagonal cross section that enables the housing 12 to cooperatively form a nonrotatable connection with a wrench (not shown).

Piston 14 and piston rod 16 are formed by threading a tubular piston body 40 on the threaded end of a piston shaft 42. See FIGS. 6-9. Piston body 40 has opposite end portions 43, 44 that each make sealing contact with the barrel wall 18. One end 46 of the piston body 40 has an enlarged annularly-beveled opening 48 that extends to a central bore 50 having internal screw threads 52. A reduced diameter bore 54 extends through the other end of the piston body 40.

Piston shaft 42 includes a cylindrical attachment portion 56 at one end of the shaft having external screw threads 58 formed on a cylindrical body portion 60.

Piston rod 16 is integrally molded with the attachment portion 56 and is formed as a generally flat rod plate 62 that extends away from one side of the body portion 60 to an enlarged free end portion 64. Piston rod end portion 64 is sized and configured to enable an extraction tool to grasp the piston rod 16 and withdraw the piston 12. Illustrated rod end portion 64 has a flat bearing end surface 66 and an indentation or shallow hole 68.

A second rod plate 70 extends from the body portion 60 and extends partway along the length of first rod plate 62. Rod plate 70 adds rigidity to the piston rod 16 and helps draw out heat from the attachment portion 56 during the injection molding process.

Piston shaft 42 also includes a short axial stub 72 that extends from the other end of the shaft attachment portion 56. Stub 72 is a remnant of the manufacturing process and has no functional role in the grease sampling device 10. Stub 72 can be eliminated in other embodiments of the piston shaft 42.

To assemble the grease sampling device 10, piston body 40 is threaded onto piston shaft 42. Stub 72 is received in piston body bore 54. The piston body 40 and the shaft attachment portion 56 together cooperatively form the piston 14. The piston rod 16 is inserted into the open housing end 22 and through housing end wall opening 28 and the piston 14 is received in the housing bore 20. When assembled, the piston 14 sealingly divides the interior of the housing 12 into front and rear chambers 74a, 74b (see FIG. 2) respectively located on opposite sides the piston 14.

Use of the grease sampling device 10 to obtain a grease sample from a source of pressurized grease is described next. FIG. 10 illustrates a machine 76 that in operation has a volume of pressurized grease 78 adjacent a bearing (not shown). The body of the machine 76 includes a normally plugged threaded grease drain or relief port 80 in fluid communication with the grease 78. Drain or port 80 may be a grease drain outlet.

The machine is shut down and the grease sampling device 10 is attached to the machine by threading housing end portion 34a into the sampling port 80. A wrench can be placed over the housing 12 at the hex 38 to apply torque when removing the housing from the port. The piston 14 is placed immediately adjacent the open housing end 22, thus opening the barrel vent holes 30, 32 into housing chamber 74b. See FIG. 11. Piston rod end portion 64 is preferably outside the barrel as shown and spaced sufficiently far from the barrel to enable the extraction tool to grasp the piston rod if necessary.

The machine is then started, pressuring the grease 78. The open end of the housing 12 is in fluid communication with the grease 78 so that pressurized grease flows through the sample port 80 and into the housing 12. The piston 14 is in fluid communication with the pressurized grease 78 and so the grease applies a force on the piston 14 moving the piston 14 towards the opposite housing end 24. The front housing compartment 74a expands as a result of the piston movement and fills with grease as shown in FIG. 12. An extraction tool can be used to assist piston movement if necessary.

The piston 14 moves past the vent holes 30, 32 before reaching the housing end wall 26. As the piston 14 moves past the vent holes 30, 32, the vent holes are placed in fluid communication with the front housing compartment 74a. At this point the force applied by the grease pressure on the piston 14 falls away, the grease pressure instead acting to flow grease through the vent holes 30, 32 rather than moving the piston 14.

The vent holes 30, 32 communicate with the front housing chamber 74a and effectively remove the piston 14 from fluid communication with the source of pressurized grease when the housing 12 is filled with a grease sample 82. Grease discharge from vents 30, 32 relieve the grease pressure within the front housing chamber 74a, preventing a buildup of back pressure that would otherwise reflect back into the machine through sample port 80 if the vent holes were not present.

The filled state of the grease sampling device 10 can be detected by piston 14 becoming stationary, the flow of grease through the vent holes 30, 32 or by the length of the piston rod 16 extending out of the housing 12 indicating the piston 14 has moved past the vent holes 30, 32. Because the housing 12 is transparent the visual position of the colored piston 14 can be observed, which indicates the device 10 is filled with grease. In other embodiments the piston rod 16 can have a marking or indicia that when visible from outside the housing indicate the amount of grease in the housing.

After the flow of grease stops, the filled grease sampling device 10 is unthreaded from the machine sample port 80. A threaded end cap (not shown) is threaded on the housing end 34a, closing the housing end and retaining the grease in the housing front chamber 74a. The housing end wall opening 28 is preferably sized to permit the piston shaft 30 to be unthreaded from the piston body if desired and removed through the opening 28. Vent holes 30, 32 may also function as tool insertion ports for a tool that grasps the piston body and prevents rotation of the piston body as the piston shaft 42 is being unthreaded from the piston body 40.

A second threaded end cap (not shown) can then be threaded on the housing end 34b to close the wall opening 28, if so desired to prevent separated oil or particularly fluid greases from exiting the housing 12. The second cap preferably extends over the vent holes 30, 32 to prevent the grease sample in the housing 12 from leaking out the vent holes. Alternatively, the piston assembly 14 can be advanced forward slightly before the end cap is threaded on the housing end 34a, to use the piston body 40 to seal the vents 30 and 32.

Removal of the grease sample from the filled grease sampling device 10 is preferably accomplished by moving the piston 14 back to the open housing end 22 and pushing the grease out from the housing. Piston shaft 30 is reattached to the piston body 40 if necessary to re-form the piston 14. A user can manually grasp and push on the exposed piston rod 16 or a mechanical drive member can engage against the rod bearing surface 66 to push the piston rod towards the open housing end 20. Piston rod indentation 68 is provided to assist in locating the drive member against the piston rod.

In the illustrated embodiment the housing bore 20 has an internal diameter of 0.315 inches and an axial length of 1.812 inches. The piston 14 has an axial length of 0.330 inches, making the volume of the grease sample in a filled device 10 about 0.12 cubic inches. The vent holes 30, 32 each have an inner diameter of 0.125 inches. These dimensions may of course be modified as necessary for other embodiments.

Grease collection device 10 may also be used as a syringe to extract a grease sample from an exposed body of grease. The piston 14 is placed at the open end 22 of the housing 12 as previously described. The open end 22 of the housing 12 is placed against the body of grease and, by pulling on the exposed piston rod 16, the piston 14 is moved towards the closed housing end 24. The piston 14 generates suction that assists in drawing in grease into the front housing chamber 74a.

When the grease sampling device 10 is used as a syringe, the relief holes 30, 32 do not perform a pressure relief function. The vent holes 30, 32 may still be used as tool insertion ports for grasping the piston body 40 when unthreading the piston shaft 42.

Figure 13:
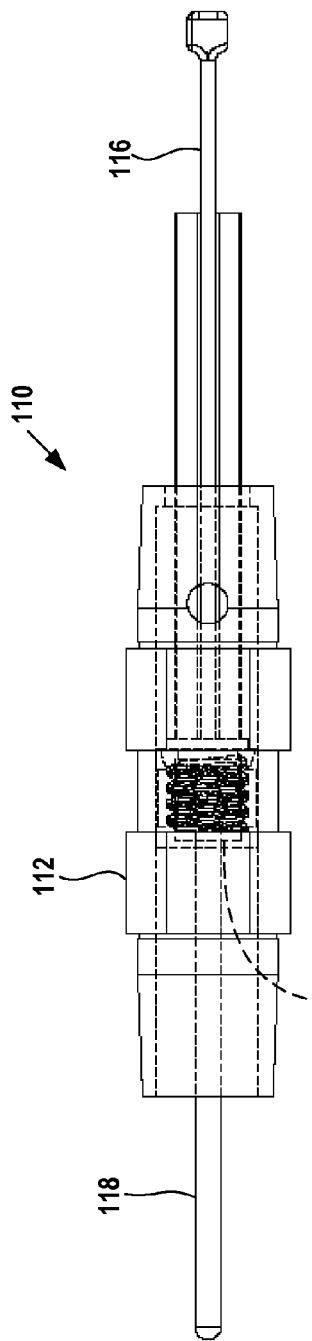
FIG. 13 is a side view of a second embodiment grease sampling device in accordance with the present invention.

FIG. 13 illustrates a second embodiment grease sampling device 110 formed from the kit's component parts. Grease sampling device 110 obtains a grease sample from adjacent a rigid bearing surface as will be explained in greater detail later.

Grease sampling device 110 includes a tubular housing or barrel 112 and a piston 114 slideably mounted in the housing 112. A piston rod 116 extends from one side of the piston 114 and out of the housing 112. An elongate push rod 118 extends from the other side of the piston 114.

Housing 112 is identical to the housing 12 and so will not be described in further detail.

Piston 114, piston rod 116, and push rod 118 are formed by threading a tubular piston body 120 onto a piston shaft 122. Piston body 120 is identical to the piston body 40 and so also will not be described in further detail.

Figure 14:
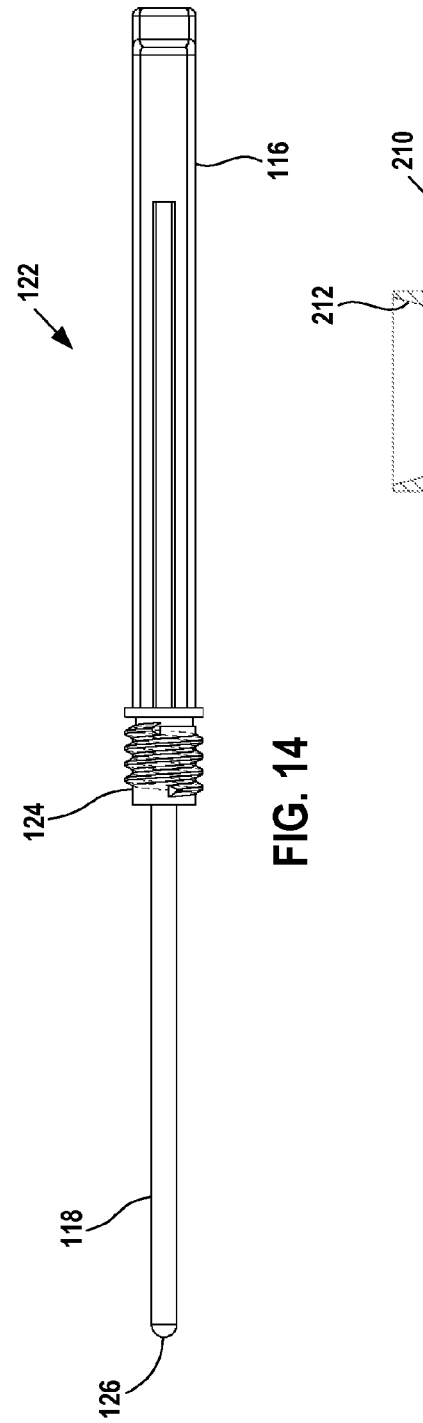
FIG. 14 is a side view of the piston shaft of the grease sampling device shown in FIG. 13.

Piston shaft 122 has a threaded attachment portion 124 identical to the attachment portion 56 and a piston rod 116 identical to piston rod 16 extending from the attachment portion 124. See FIG. 14.

Push rod 118 is integrally formed with the attachment portion 124 and extends away from the opposite side of the attachment portion 124 from the piston rod 116. Push rod 118 is formed with a generally circular cross section and extends to a free rod end 126. The push rod 118 is closely received within the reduced diameter bore of the piston body 114 when the piston body 114 is threaded onto the piston shaft 122. The length of the push rod 118 is such that the push rod 118 is fully within the housing 112 when the piston 114 abuts against the partially closed end of the housing 112.

Use of the grease sampling device 110 from adjacent a rigid bearing surface is described next. FIG. 15 illustrates a machine housing 127 containing a bearing component (not shown). The bearing component has a rigid bearing surface 128 that supports a layer of grease 130 on the surface. Housing 127 includes a normally-closed access port or opening 131 that can receive the grease sampling device 110. It is desired to obtain a representative grease sample from grease adjacent the bearing surface 128 with the grease sampling device 110.

The grease sampling device 110 is assembled from the housing 112, piston body 120, and piston shaft 122. The piston 114 is placed at the open end 132 of the housing 112 so that the piston 114 closes the open end of the housing and the push rod 118 extends its full length out of the housing 112 as shown in FIG. 16. Preferably the piston rod has sufficient axial length to place the enlarged end of the piston rod outside the barrel and sufficiently spaced from the end of the barrel to enable an extraction tool to grasp the piston rod when the piston 114 is at the open end of the housing.

The open end 132 of the housing 112 is inserted into the grease 130 and moved towards the bearing surface 128. See FIG. 16. To extend the reach of the housing into the internal machine space, an elongate hollow extension tube with an internal female thread can be engaged onto the threaded section 36 of the partially closed end of the housing.

The illustrated grease layer 130 has a thickness greater than the length of the push rod 118. The open end of the housing 112 contacts the grease away from the bearing surface 128. By placing the piston 114 at the opening 132, the piston 114 prevents unrepresentative grease away from the bearing surface from entering the grease sampling device 110.

The grease sampling device 110 is moved towards the bearing surface 128 until the free end of the push rod 118 makes initial contact with the bearing surface 128. See FIG. 17. The piston 114 has prevented grease from entering the housing 112 as the device 110 moves through the grease 130 to the position shown in FIG. 17 with the housing 112 spaced the length of the push rod 118 above the bearing surface.

Continued movement of the housing 112 towards the bearing surface 128 forces the piston 114 to move towards the closed housing end until the housing 112 comes against the bearing surface 128. See FIG. 18. Relative movement of the piston 114 within the housing 112 enables the grease adjacent the bearing surface to enter the front housing chamber 134. Suction generated by the movement of the piston 114 assists in drawing the grease into the housing chamber 134. If necessary, an extraction tool can be used to grasp the piston rod and assist in movement of the piston.

Device 110 is removed from the grease 130 after the housing 112 engages the bearing surface 128. The grease sample is held within the housing chamber 134. The housing end 34*a* is capped as previously described to retain the grease sample in the housing 112. The piston shaft 122 is unthreaded and removed from the piston body 120 before capping the other end of the housing 112. Although the housing vent holes do not perform a pressure relief function when the housing forms part of the grease sampling device 110, the vent holes may still be used as tool insertion ports for grasping the piston body 120 when unthreading the piston shaft 122.

A piston shaft 42 can be reattached to the piston body 120 to form a piston without a push rod for pushing the grease sample out of the housing 112.

FIG. 19 illustrates a grease sampling kit 210 having component parts for making the grease sampling devices 10 and 110. The kit 210 includes a number of housings 12, piston bodies 40, first piston shafts 42, and second piston shafts 120. A grease sampling device 10 or a grease sampling device 110 may be quickly assembled by selecting the appropriate component parts. This enables the user to put together different grease devices that each best fits the conditions under which a grease sample is to be obtained.

Figure 20:
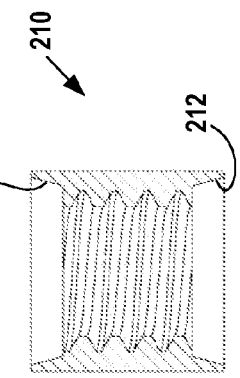
FIG. 20 is a sectional view of a second embodiment piston body

FIG. 20 illustrates a second embodiment piston body 210 that can be used in place of piston body 40. Piston body 210 is similar to piston body 40 but includes enlarged annularly beveled openings 212 on both axial ends of the body. This enables either end of the piston body 210 to be threaded onto a piston shaft 42 or a piston shaft 122. The tapered surface of the opening 212 facing the front housing chamber forms a lip seal against the housing wall when the chamber is filled with pressurized grease that resists leakage of grease past the piston.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A method of obtaining a grease sample from a source of grease under pressure, the method comprising the steps of:
   (a) providing a tubular housing having an open end and a piston in the housing, the piston and housing axially movable with respect to each other, the piston positioned to be movable away from the open end of the housing;
   (b) fluidly connecting the open end of the housing to the source of pressurized grease to flow grease to the opening;
   (c) flowing the pressurized grease through the open end of the housing and into the housing, the flow of grease into the housing generating a force against the piston moving the piston away from the open end of the housing; and
   (d) fluidly disconnecting the piston from the source of pressurized grease while maintaining the fluid connection between the source of pressurized grease and the open end of the housing, the disconnect occurring after the piston has moved away from the open end of the housing after accumulating a volume of grease in the housing.

2. The method of claim 1 wherein the piston divides the housing interior into a first chamber adjacent the open housing end and a second chamber, the housing comprises a relief vent extending through the housing wall, the piston movable between a first operating position wherein the relief port is in fluid communication with the second chamber and a second operating position wherein the relief vent is in fluid communication with the first chamber, the method further comprising the steps of:
   (e) positioning the piston in the first operating position when fluidly connecting the open end of the housing to the source of pressurized grease;
   (f) flowing the pressurized grease into the first chamber, the grease moving the piston from the first operating position to the second operating position; and
   (g) fluidly connecting the relief vent to the source of high pressure grease when the piston has moved to the second operating position to fluidly disconnect the piston from the source of high pressure grease.

3. The method of claim 2 comprising the step of:
   (h) flowing grease out of the relief vent when the piston has moved to the second operating position to resist a buildup of back pressure upstream from the housing.

4. A method of obtaining a grease sample from a source of grease under pressure, the method comprising the steps of:
   (a) providing a tubular housing having an open end and a piston movable in the housing, the piston dividing the housing interior into a first chamber adjacent the open housing end and a second chamber, the housing comprising a relief vent extending through the housing wall, the piston movable between a first operating position wherein the relief port is in fluid communication with the second chamber and a second operating position wherein the relief vent is in fluid communication with the first chamber;

(b) fluidly connecting the open end of the housing to the source of pressurized grease to flow grease to the opening and positioning the piston in the first operating position when fluidly connecting the open end of the housing to the source of pressurized grease;

(c) flowing the pressurized grease through the open end of the housing and into the housing, the grease engaging the piston and pushing the piston away from the open end of the housing from the first operating position to the second operating position; and (d) fluidly disconnecting the piston from the source of pressurized grease after the piston has moved away from the open end of the housing after accumulating a volume of grease in the housing by fluidly connecting the relief vent to the source of high pressure grease when the piston has moved to the second operating position.

5. The method of claim 4 comprising the step of:

(h) flowing grease out of the relief vent when the piston has moved to the second operating position to resist a buildup of back pressure upstream from the housing.

* * * * *